United States Patent [19]

Medem et al.

[11] Patent Number: 4,774,221

[45] Date of Patent: Sep. 27, 1988

[54] SUPPORTED HYDROGENATION CATALYSTS

[75] Inventors: Harald Medem, Krefeld; Udo Birkenstock, Ratingen; Herbert Schmidt, Leverkusen; Burkhard Lachmann, Meerbusch, all of Fed. Rep. of Germany

[73] Assignee: Bayer Aktiengesellschaft, Leverkusen, Fed. Rep. of Germany

[21] Appl. No.: 921,034

[22] Filed: Oct. 20, 1986

[30] Foreign Application Priority Data

Oct. 26, 1985 [DE] Fed. Rep. of Germany ....... 3538129

[51] Int. Cl.⁴ .................... B01J 23/44; B01J 23/58
[52] U.S. Cl. .................... 502/327; 502/177; 502/178; 502/243; 502/262; 502/333; 502/524
[58] Field of Search ............... 502/243, 262, 327, 328, 502/330, 333, 177, 178

[56] References Cited

U.S. PATENT DOCUMENTS

| | | | |
|---|---|---|---|
| 3,007,941 | 11/1961 | Copelin et al. | 502/243 |
| 3,076,810 | 2/1963 | Duggan et al. | 568/835 |
| 3,435,090 | 3/1969 | Abell, Jr. et al. | 502/333 |
| 3,816,344 | 6/1974 | Shimizu et al. | 502/333 |
| 3,932,514 | 1/1976 | Thelen et al. | 502/333 |
| 4,162,267 | 7/1979 | Fisher et al. | 568/835 |
| 4,212,990 | 7/1980 | Yasuhara | 568/835 |
| 4,258,268 | 3/1981 | Bjornson | 568/835 |
| 4,407,733 | 10/1983 | Birkenstock et al. | 502/174 |
| 4,410,741 | 10/1983 | Peppen | 568/835 |

*Primary Examiner*—Carl F. Dees
*Attorney, Agent, or Firm*—Sprung Horn Kramer & Woods

[57] ABSTRACT

Supported catalysts containing palladium on a support material are improved by added bases which remain on the material. These supported catalysts are useful for hydrogenating optionally substituted phenols to give the corresponding cyclohexanols as the predominant product.

6 Claims, No Drawings

SUPPORTED HYDROGENATION CATALYSTS

The present invention relates to improved supported catalysts, to the preparation thereof and to a process for the hydrogenation of phenols to give the corresponding cyclohexanols, using such supported catalysts.

Supported catalysts are to be understood as compositions containing catalytically active substances, for example metals as such or in the form of compounds, on supporting materials, for example silicon dioxide, aluminum oxide, magnesium silicates or carbonates and aluminum silicates or carbonates. Catalysts containing the noble metals on supports having a low BET surface area, for example a surface area less than 50 $m^2/g$, have acquired a special importance. These catalysts can be obtained, for example, by impregnating the supporting material with an aqueous solution of noble metal salts, followed by reduction.

For example, palladium-containing supported catalysts and their use in the hydrogenation of phenol to cyclohexanone are described in DE-OS (German Published Specification) No. 2,045,882, in the preparation of which aluminum spinel supporting materials, such as lithium, magnesium, cobalt, manganese or zinc spinels, which have been calcined at a high temperature are employed. In such catalysts, the catalytically active substances are generally distributed irregularly over the whole supporting material. As a consequence of this, when these catalysts are employed industrially, undesirable differences in activity, selectivity of conversion and service life can occur. Furthermore, it frequently happens that substances present near to the centre of a support particle have either no influence at all or only a minor influence on the reaction to be catalyzed. In the case of valuable catalytically active substances, for example in the case of noble metals and compounds thereof, this results in unnecessarily high catalyst costs.

Attempts have, therefore, already been made to prepare catalysts in which supporting materials having a small BET surface area contain the catalytically active substances only within a narrow, external region of the support particles. Processes of this type are described, for example, in DE-OS (German Published Specifications) Nos. 1,944,933, 2,517,313, 2,317,536 and 2,715,094, U.S. Pat. Nos. 3,271,327 and 2,946,829 and British Pat. specification No. 1,283,737.

However, all these processes and the catalysts obtainable thereby still suffer from considerable disadvantages. Thus the supporting materials employed for the preparation of the catalysts are, by virtue of their surface characteristics, generally not inert and hence, when employed industrially, as a rule cause the formation of undesirable by-products, particularly in the case of large inner surfaces. A further disadvantage in the use of the catalysts prepared in this way consists in the fact that abrasion losses and poisoning occur very easily with the noble metals which are deposited in a very high concentration on the outer surfaces of the support particle. For this reason only inadequate catalyst service lives are obtained in many cases.

EP-OS (European Published Specification) No. 0,012,153 describes, inter alia, supported catalysts in which an inert supporting material having a BET surface area less than 20 $m^2/g$ is impregnated to saturation with a solution of a base, then dried to constant weight, then impregnated with a metal salt solution, also until saturation is reached, and finally reduced to the metal, the base being applied in an amount such that, before impregnation with the metal salt solution, 0.01 to 50 gram equivalents of base per gram equivalent of metal are present in the supporting material. Catalysts prepared by this process contain the catalytically active substances within a narrow, annular zone in the interior of the inert supporting material, that is to say immediately below the surface of the support particles, as a result of which the catalytically active substances are, on the one hand, largely protected from poisoning and losses through abrasion, but, on the other hand, are deposited in a region of the supporting material which can still be reached readily by the reactants.

When a supported catalyst of this type, containing 9 g of palldium per liter of $\alpha$-$Al_2O_3$ support having a BET surface area of 9.8 $m^2/g$, was employed for the hydrogenation of phenol, a reaction product containing 96.2% by weight of cyclohexanone and 3.7% by weight of cyclohexanol was obtained in accordance with Example 72 of EP-OS (European Published Specification) No. 0,012,153.

Frequently, however, the formation of cyclohexanols is desired, since cyclohexanol and derivatives thereof are also of importance on a large industrial scale. Cyclohexanol itself is required, for example, as a starting material for the preparation of adipic acid, a primary material of the chemical industry which is also important (see, for example, Kirk-Othmer, Encyclopedia of Chemical Technology, 2nd edition, Volume 6, page 685). Various esters of cyclohexanol are also of importance on a large industrial scale, for example dicyclohexyl phthalate and adipate, as plasticizers for plastics, cyclohexyl acetate as a solubilizer and cyclohexyl acrylate as a comonomer for polymerization reactions. Other cyclohexanol derivatives, for example methylcyclohexanol and trimethylcyclohexanol are employed as solvents and emulsifiers in the paint and textile industries (see, for example, Ullmanns Enzyklopadie der techn. Chemie ("Ullmann's Encyclopedia of Industrial Chemistry"), 4th edition, Volume 9, pages 692–693). Finally, perhydrobisphenol is an important starting component in polycondensation reactions (see, for example, Ullmanns Enzyklopadie der techn. Chemie ("Ullmann's Encyclopedia of Industrial Chemistry"), 4th edition, Volume 7, page 229).

Supported catalysts have now been found which can be obtained by, successively:

(a) impregnating an inert supporting material having a BET surface area less than 20 $m^2/g$ with a base until saturation is reached, (b) drying the material to constant weight, (c) impregnating it with a palladium salt solution until saturation is reached, (d) washing it with water until ions from the compounds used up to this point can no longer be detected in the wash water, and (e) drying, and which are characterized in that they can be obtained by subsequently (f) applying a base in a quantity such that the catalyst contains 0.01 to 50 gram equivalents of base per gram equivalent of palladium, (g) drying to constant weight and (h) reducing the deposited palladium compounds to the metal at any desired point in time after carrying out stage (c) and before carrying out the reaction to be catalyzed by means of the catalyst, and, if carrying out this reduction after stage (f), doing so under conditions in which the base applied in stage (f) remains on the catalyst.

Supported catalysts which can be obtained by carrying out stages (a) to (e) are known and are described in detail, for example, in EP-OS (European Published Specification) No. 0,012,153. In the followiing text, therefore, stages (a) to (e) will only be described briefly.

The inert supporting material to be used in stage (a) can be, for example, metal oxides, silicates, spinels, carbides, carbonates or mixtures thereof. Preferred supporting materials are aluminum oxides, silicon dioxides, silicon dioxide/aluminum oxide mixtures, amorphous silicas, kieselguhrs, barium, strontium or calcium carbonates, mixtures thereof optionally containing, in addition, silicon dioxides or aluminum oxides, titanium oxides, zirconium oxides, magnesium oxides, magnesium silicates, zirconium silicates, magnesium/aluminum spinels, silicon carbides, tungsten carbides, mixtures of silicon carbides with silicon dioxides, or any desired mixtures of the abovementioned materials. Aluminum oxide, especially $\alpha$-$Al_2O_3$, is particularly preferred. The supporting materials can be used in a very wide variety of forms, for example as spheres, granules, extrudates, tablets, saddle-shaped bodies, tubular sections, fragments and/or honeycomb ceramics. The inert supporting material preferably has a BET surface area less than 10 $m^2$/g.

The base to be used in stage (a) can be, for example, an oxide, carbonate, bicarbonate, hydrogenphosphate, hydroxide, alkoxide, formate, alkali metal silicate, alkali metal aluminate or mixtures thereof. Alkali metal hydroxides and/or alkali metal carbonates are preferred.

Bases are preferably employed in a dissolved form, is being possible to use water or organic solvents, for example alcohols or ketones, as the solvent. Aqueous solutions of alkali metal hydroxides are preferred for this purpose.

The base can be used in stage (a), for example, in an amount such that, after stage (a), 0.01 to 50 gram equivalents of base, preferably 0.5 to 20 gram equivalents of base, are present in the supporting material per gram equivalent of elementary or combined palladium present in the supporting material after stage (c).

The drying in stage (b) can be carried out, for example, at 50° to 200° C. in a drying cabinet or in a stream of hot air.

In stage (c) it is preferable to use a solution of a commercially available simple or complex palladium salt. Aqueous solutions of $Na_2[PdCl_4]$, $PdCl_2$ and/or $Pd(NO_3)_2$ are preferred. The concentration of such a solution can, for example, be such that sufficient palladium compounds are applied to the support in a single impregnation for the support to contain thereafter, per liter, 1 to 20 g of palladium in elementary or combined form.

The washing in stage (d) serves the purpose of removing soluble ions still present on the support. These can be, for example, ions of the base employed and/or anions of the palladium salt employed. In general, it is advantageous to observe a waiting time of, for example, 2 hours to 3 days between stage (c) and stage (d).

The drying in stage (e) can be carried out in the same way as that in stage (b).

It is an essential characteristic of the supported catalysts according to the invention that they can be obtained by subsequently doping, after the application of palladium under defined conditions (see stages (d) and (e)), a specific amount of base which remains on the catalyst up to and including the time when it is used.

Examples of bases suitable for stage (f) are oxides, hydroxides, alkoxides, carbonates, bicarbonates, hydrogenphosphates, formates, silicates and/or aluminates of, for example, alkali and/or alkaline earth metals, particularly preferably of lithium, potassium, magnesium, calcium, strontium and/or barium. Hydroxides and oxides thereof, such as lithium hydroxide, potassium hydroxide, magnesium oxide, calcium hydroxide, strontium hydroxide and barium hydroxide, are particularly preferred. Barium hydroxide is very particularly preferred.

In stage (f) the base is generally applied by impregnation in the form of a solution. Suitable solvents are water or organic solvents, for example alcohols or ketones. Water is preferred. The bases can, however, also be applied as such, if so, preferably in a finely divided form or as a mixture with any desired liquid phase in which the base must be insoluble or not completely soluble.

It is preferable to apply, in stage (f), 0.01 to 50 gram equivalents of base per gram equivalent of palladium present on the catalyst.

Stage (g) can be carried out in the same manner as stages (b) and (e).

Before the catalyst according to the invention can be used, the palladium compounds located on it still have to be reduced to metal stage (h)). This reduction can be carried out at any desired point in time after stage (c) has been carried out and before the reaction to be catalyzed by means of the catalyst has been carried out. This reduction is preferably carried out immediately subsequently to stage (c) or in situ, that is to say immediately before carrying out the reaction to be catalyzed by means of the catalyst. This reduction can be carried out in the manner which is in itself known and using reducing agents which are customary for reductions of this type. Examples of suitable reducing agents are hydrazine hydrate, hydrogen, formaldehyde and sodium borohydride. Preferred reducing agents are gaseous hydrogen and aqueous hydrazine hydrate.

Since it is a characteristic essential to the invention that the finished catalyst still contains the base applied to stage (f), care must be taken that, if reduction is carried out after stage (f), the base applied in stage (f) remains on the catalyst. In such cases, that is to say, for example, in the case of the abovementioned in situ reduction, it is therefore not possible to employ aqueous solutions of reducing agents. Reduction is then preferably carried out by means of gaseous hydrogen.

It is also possible to carry out repeated treatments with reducing agents, for example subsequently to stage (c) and in situ (the latter as previously described).

The supported catalysts according to the invention can be used for a very wide variety of reactions catalyzed by noble metals, in particular for hydrogenation and dehydrogenation reactions. The supported catalysts according to the invention can be employed in catalytic reactions either in the liquid phase or in a down-flow liquid phase or in the gas phase. The down-flow liquid phase and the gas phase are preferred. The reaction can be carried out either under normal pressure or under an excess pressure. Catalytic hydrogenation reactions are a preferred field of use for the supported catalysts according to the invention. They are particularly suitable for hydrogenating aromatic systems in the nucleus and for hydrogenating certain substituents, for example nitro groups on aromatic systems. The supported catalysts according to the invention are preferably used in the catalytic hydrogenation of phenol and substituted phenols, it being possible to hydrogenate the aromatic system and/or the substituent. The use, which is particularly preferred, of supported catalysts according to the invention in the hydrogenation of phenols to give cyclohexanols, is a further subject of the present invention and is described in detail later in the text.

The present invention also relates to a process for the preparation of supported catalysts in which, successively (a) an inert supporting material having a BET surface area less than 20 m$^2$/g is impregnated to saturation with a base,
(b) is dried to constant weight,
(c) is impregnated to saturation with a palladium salt solution,
(d) is washed with water until ions from the compounds used up to this point can no longer be detected in the wash water, and
(e) is dried, which is characterized in that, thereafter (f) a base is applied in a quantity such that the catalyst contains 0.01 to 50 gram equivalents of base per gram equivalent of palladium,
(g) the catalyst is dried to constant weight, and
(h) the deposited palladium compounds are reduced to the metal at any desired point in time after carrying out stage (c) and before carrying out the reaction to be catalyzed by means of the catalyst, and, if this reduction is carried out after stage (f) it is carried out under conditions in which the base applied in stage (f) remains on the catalyst.

The suitable and preferred measures described earlier in the text, by means of which supported catalysts according to the invention can be obtained, are also suitable and preferred in the process according to the invention for the preparation of supported catalysts.

Finally, the present invention also relates to a process for the hydrogenation of optionally substituted phenols to give cyclohexanols, which is characterized in that it is carried out in the presence of supported catalysts which can be obtained by, successively:

(a) impregnating an inert supporting material having a BET surface area less than 20 m$^2$/g with a base until saturation is reached,
(b) drying the material to constant weight,
(c) impregnating it with a palladium salt solution until saturation is reached,
(d) washing it with water until ions from the compounds used up to this point can no longer be detected in the wash water,
(e) drying,
(f) applying a base in a quantity such that the catalyst contains 0.01 to 50 gram equivalents of base per gram equivalent of palladium,
(g) drying to constant weight and
(h) reducing the deposited palladium compounds to the metal at any desired point in time after carrying out stage (c) and before carrying out the reaction to the catalyzed by means of the catalyst, and, if carrying out this reduction after stage (f), doing so under conditions in which the base applied in stage (f) remains on the catalyst.

Examples of phenols which can be employed in the hydrogenation process according to the inventin are those of the formula (I)

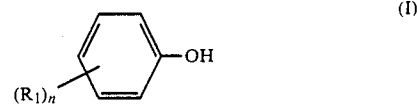

in which
R$_1$ represents C$_1$ to C$_6$ alkyl, C$_6$ to C$_{10}$ aryl, hydroxyl, nitro, halogen, optionally substituted amino, C$_1$ to C$_6$ alkoxy or C$_6$ to C$_{10}$ aroxy and
n represents zero or an integer from 1 to 5,
but, in the event that R$_1$=nitro, n only represents zero, 1 or 2.

Halogen here can denote fluorine, chlorine, bromine or iodine, optionally substituted amino, for example an NH$_2$ group which is optionally monosubstituted or disubstituted by C$_1$ to C$_6$ alkyl or C$_6$ to C$_{10}$ aryl. If several radicals R$_1$ are present, that is to say if n represents 2, 3, 4 or 5, these R$_1$ radicals can be identical or different.

R$_1$ preferably represents methyl, ethyl, n-propyl, i-propyl, n-hexyl, phenyl, hydroxyl, chlorine, bromine, NH$_2$, methoxy, ethoxy or phenoxy and n preferably represents zero, 1 or 2.

It is particularly preferable for R$_1$ to represent methyl in the meta-position and/or para-position and for n to represent zero or 1.

It is also possible, for example, to employ phenols of the formula (II)

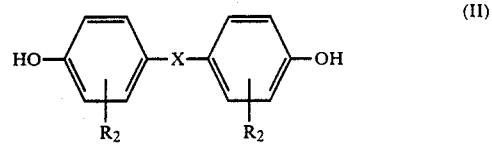

in which
the R$_2$s independently of one another each represent hydrogen, C$_1$ to C$_6$ alkyl, C$_1$ to C$_6$ alkoxy or halogen and
X represents —CH$_2$—, —C(CH$_3$)$_2$—, —cyclohexyl—, —CO—, —S—, —SO$_2$—, —O— or a single bond.

R$_2$ preferably represents hydrogen or methyl and X preferably represents —C(CH$_3$)$_2$—.

The use of phenols of the formula (I) is preferred to the use of phenols of the formula (II).

The hydrogenation process according to the invention is preferably carried out using catalysts which can be obtained by the measures indicated as advantageous earlier in the text (in the description of the catalysts according to the invention). It is particularly preferable to employ, in the hydrogenation process according to the invention, catalysts containing α-Al$_2$O$_3$ as the inert supporting material and barium hydroxide as the base.

In other respects the hydrogenation process according to the invention can be carried out under customary reaction conditions and in customary reactors. For example, the hydrogenation according to the invention can be carried out with readily vaporizable phenols in the gas phase and in tubular reactors and with phenols which are difficult to vaporize the down-flow liquid phase and in vertical reactors. The reaction temperatures can be, for example, between 100° and 350° C. They are preferably between 120° and 250° C. The pressure during the reaction can be, for example, between 1 and 350 bar. When the reaction is carried out in the gas phase, relatively low pressures, for example pressures within the range from 1 to 5 bar, are generally preferred. When the reaction is carried out in the downflow liquid phase, relatively high pressures, for example pressures within the range from 100 to 350 bar, are generally preferred. In general, at least 2 moles of hydrogen are fed to the reactor per mole of the particular phenol employed. It is preferable to introduce into the reactor 4 or 12 moles of hydrogen per mole of the particular phenol employed. When the hydrogenation according to the invention is carried out in the gas phase, the procedure followed is, for example, to vaporize the phenol in the feed stream of hydrogen and then to pass this combined stream into the reactor. If catalysts in which it is still necessary to reduce the palladium compounds present before the admission of a phenol are employed in the hydrogenation process according to the invention, this reduction can be carried out in a particularly simple manner by first allowing only hydrogen to flow over the catalyst located in the reactor and not introducing the particular phenol until the palladium compounds have been reduced.

The products leaving the reactor are generally cooled, and the hydrogenated phenols are separated off in a liquid or solid form. They can, if appropriate, be purified further by customary methods, for example by distillation. The excess of hydrogen which is generally present can be recycled to the reactor, it being preferable to discharge a small proportion.

The hydrogenation, according to the invention, of phenols by means of the supported catalysts according to the invention surprisingly affords products containing, very preponderantly, in general to the extent of over 90% by weight and frequently to the extent of over 95% by weight, the corresponding cyclohexanols, and only very little, in general less than 8%, of the corresponding cyclohexanones. The formation of other by-products is very slight; the service lives of the catalysts to be employed are high.

This very preponderant formation of cyclohexanols could not have been expected, above all because, in accordance with the state of the art, when catalysts containing palladium are doped, precisely the opposite takes place, namely a further promotion of the formation of cyclohexanones at a high level and a further repression of the formation of cyclohexanols at a low level.

For example, DE-AS (German Published Specification) No. 1,298,098 describes the preparation of cyclohexanone by hydrogenating phenols in the presence of catalysts containing, besides palladium, alkaline earth metal hydroxides on $\gamma$-Al$_2$O$_3$ supports, mixtures containing 88 to 95% by weight of cyclohexanone and 2 to 6% by weight of cyclohexanol being obtained. In contrast with the present invention, however, the supporting material employed in accordance with DE-AS (German Published Specification) No. 1,298,098 is $\gamma$-Al$_2$O$_3$, that is to say a supporting material having a BET surface area of approximately 100 to 300 m$^2$/g.

DE-OS (German Published Specification) No. 2,752,291 also describes the hydrogenation of phenol to give cyclohexanone. In this case catalysts consisting of carbon or charcoal particles coated with palladium and having an (inner) surface area of 100 to 2,000 m$^2$/g, and a phenol containing a small amount of alkali compounds are employed. Based on the interaction of the promoter contained in the phenol with the catalyst, the effect achieved is, for example, that, after a hydrogenation time of 210 minutes, a product containing 1.1% by weight of cyclohexanol, 87.5% by weight of cyclohexanone and 11.4% by weight of phenol is obtained, whereas, if the promoter in the feed phenol is omitted under otherwise identical conditions, a product containing 1.4% by weight of cyclohexanol, 65.9% by weight of cyclohexanone and 32.5% by weight of phenol is obtained (see Example 1 in DE-OS (German Published Specification) No. 2,752,291). In contrast with the present invention, here too a support having a large internal surface area is employed, this time based on charcoal.

Finally, hydrogenations of phenol are also described in U.S. Pat. No. 3,076,810. It is proved by means of examples that, using a phenol containing 0.01 part of sodium carbonate in 1,000 parts and using a catalyst containing 5% of palladium on charcoal, as well as 5,000 ppm of sodium, a product mixture having the composition 97.2% of cyclohexanone, less than 0.5% of phenol and remainder cyclohexanol is obtained (see Example 1A). Varying the amount of sodium in the catalyst alters the cyclohexanol content (maximum approximately 3%) in the product only to an immaterial extent (see Examples 1B and 1D). Products having a high content of cyclohexanol (maximum 80%) are only obtained if a palladium/charcoal catalyst doped with sodium and a phenol containing a relatively large proportion of sodium carbonate are employed (see Example 4). This state of the art also leads away from the present invention, since it suggests that the feed phenol, and not the catalyst, should be varied in order to increase the selectivity of conversion to cyclohexanol. In addition, selectivities of conversion to cyclohexanol which are even markedly higher than 80% are achieved using catalysts according to the invention.

The following examples serve to illustrate the invention further, without limiting it in any way.

EXAMPLES (A) Description of the supporting materials employed

TABLE 1

| Support No. | Composition of the support | Geometrical form: shape | BET Surface area ($M^2$/g) | Bulk Density (g/l) | Water absorption (ml/100 g) |
|---|---|---|---|---|---|
| 1 | Al$_2$O$_3$ | Spheres, 3–6 mm | 9.8 | 812 | 45.1 |
| 2 | Al$_2$O$_3$ <5% SiO$_2$ | Extrudate, 5 mm $\phi$ | 6.0 | 1,075 | 26.4 |
| 3 | Al$_2$O$_3$ | Tablets, 5 × 5 mm | 8.5 | 562 | 85.0 |
| 4 | Al silicate ~85% of Al$_2$O$_3$ ~15% of SiO$_2$ | Granules, 3–5 mm $\phi$ | 4.5 | 1,190 | 22.4 |
| 5 | Mg/Al silicate ~53% of Al$_2$O$_3$ ~32% of SiO$_2$ ~15% of MgO | Spheres 6 mm $\phi$ | 2.1 | 1,060 | 21.0 |
| 6 | Al/silicate ~88% of SiO$_2$ | Spheres, 8 mm $\phi$ | 1.0 | 1,000 | 28.6 |

TABLE 1-continued

| Support No. | Composition of the support | Geometrical form: shape | BET Surface area (M²/g) | Bulk Density (g/l) | Water absorption (ml/100 g) |
|---|---|---|---|---|---|
| 7 | ~12% of Al$_2$O$_3$ Zr/Mg silicate ~88% of SiO$_2$ ~6% of ZrO$_2$ Remainder Al$_2$O$_3$ | Spheres 8 mm φ | 5.6 | 1,050 | 12.4 |
| 8 | SiO$_2$ <5% Al$_2$O$_3$ | Spheres 5 mm φ | 10.0 | 834 | 27.0 |
| 9 | SiO$_2$ | Tablets 3 × 3 mm | 6.5 | 1,132 | 11.0 |

(B) Preparation of the catalysts (a) General description of the preparation of catalysts 1,000 ml of a support from Table 1 were impregnated to saturation at room temperature with a solution containing the required amount of base in a revolving drum. The volume of the impregnating solution was calculated from the absorbency and bulk density of the support. The impregnating solution accordingly employed was completely absorbed by the particular support in the course of a few minutes. The support thus impregnated was dried to constant weight in a revolving drum or in another suitable vessel in a hot stream of gas, if appropriate an inert gas, at up to 200° C.

The dry support which had been pretreated in this way was again impregnated in accordance with its absorbency with a solution containing the required amount of palladium salt, as described above. After this impregnation, the moist support was poured into a suitable, closable vessel and was left therein for up to several days. The support thus treated was then washed with water until free from alkali and was dried.

The support thus obtained was impregnated in accordance with its absorbency with a solution containing the required amount of base, as described above, and was then dried to constant weight.

(b) Example 1

1 l of the α-alumiunum oxide support No. 1 (see Table 1) was impregnated with 366 ml of an aqueous solution containing 10.8 g, corresponding to 0.27 gram equivalent, of NaOH. The solution was completely taken up by the support in the course of a few minutes. The moist support was poured into a vertical glass tube of capacity 2 l and was dried to constant weight in a stream of hot air at 120° C. and at an air rate of 25 Nm³ of air per hour.

The dry support which had been pretreated in this way was impregnated in accordance with its absorbency with 366 ml of an aqueous sodium tetrachloropalladate-(II) solution containing 9 g of palladium, corresponding to 0.169 gram equivalent, and was transferred while moist into an appropriately sized, closable vessel.

The amount of NaOH present in the support corresponded to an equivalence ratio (g. equivalent of NaOH:g. equivalent of Pd) of 1.60. After a reaction time of 2 hours, the support which had been impregnated with sodium tetrachloropalladate-(II) and pretreated with sodium hydroxide solution was washed in a flowing stream of distilled water until alkali metal ions and ions of the compounds used in its preparation could no longer be detected in the wash water, which was the case after 10 hours.

Subsequent drying was carried out in a stream of hot air as described above.

The catalyst precursor thus charged with palladium contained the palladium within a narrowly defined zone in the interior of the support and close under the surface of the support.

After this treatment, the palladium-containing catalyst precursor was impregnated with 366 ml of an aqueous impregnation liquid containing 10.0 g, corresponding to 0.063 gram equivalent, of barium hydroxide octahydrate and was dried in stream of hot air at 120° C. analogously to the drying described above.

The catalyst was then reduced in a stream of hydrogen at 180° C. The finished catalyst contained 9 g of palladium and, calculated as anhydrous hydroxide, 5.43 g of barium hydroxide per liter of support. The amount of barium hydroxide present in the catalyst corresponded to an equivalence ratio (g. equivalent of base:g. equivalent of palladium) of 0.373.

Example 2

The procedure followed was as described in Example 1, but the support which had been impregnated with sodium tetrachloropalladate-(II) was covered with 400 ml of an aqueous 10% strength solution of hydrazine hydrate before being washed and was allowed to stand for 2 hours, in order to reduce the palladium compounds deposited on the support to metallic palladium. The support containing palladium was then washed as described in Example 1, dried, impregnated with barium hydroxide octahydrate, dried again and subjected to treatment in a stream of hydrogen.

Examples 3–18

The procedure followed was as in Example 1, but the amount of NaOH, the amount of palladium and the amount and nature of the base applied after the deposition of palladium were varied. The details can be seen in Table 2.

In Table 2, "g.equ." represents gram-equivalents. The indications "Ba(OH)$_2$" and "Sr(OH)$_2$" represent Ba(OH)$_2$.8H$_2$O and Sr(OH)$_2$.8H$_2$O respectively. In the case of Example 12, the Ca(OH)$_2$ was mainly present in a suspended form.

TABLE 2

| Example No. | Catalyst precursor | | | | | | Catalyst according to the invention | | | |
|---|---|---|---|---|---|---|---|---|---|---|
| | Support No. (see Table 1) | NaOH | | | Pd in the Form of Na$_2$PdCl$_4$ | | g. equ. of NaOH per g. equ. of Pd | Base according to the invention | | g. equ. of base per g. equ. of Pd |
| | | (g) | (g) | (g. equ.) | (g) | (g. equ.) | | Type | (g) | (g. equ.) | |
| 3 | 1 | 812 | 3.0 | 0.075 | 5.0 | 0.094 | 0.80 | Ba(OH)$_2$ | 10 | 0.063 | 0.670 |
| 4 | 1 | 812 | 21.6 | 0.540 | 18.0 | 0.338 | 1.60 | Ba(OH)$_2$ | 10 | 0.063 | 0.186 |
| 5 | 1 | 812 | 10.8 | 0.270 | 9.0 | 0.169 | 1.60 | Ba(OH)$_2$ | 20 | 0.127 | 0.751 |

TABLE 2-continued

| Example No. | Catalyst precursor | | | | | | | Catalyst according to the invention | | | |
|---|---|---|---|---|---|---|---|---|---|---|---|
| | Support No. (see Table 1) | NaOH | | | Pd in the Form of Na$_2$PdCl$_4$ | | g. equ. of NaOH per g. equ. of Pd | Base according to the invention | | | g. equ. of base per g. equ. of Pd |
| | | (g) | (g) | (g. equ.) | (g) | (g. equ.) | | Type | (g) | (g. equ.) | |
| 6 | 1 | 812 | 10.8 | 0.270 | 9.0 | 0.169 | 1.60 | KOH | 10 | 0.178 | 1.053 |
| 7 | 1 | 812 | 21.6 | 0.540 | 18.0 | 0.338 | 1.60 | KOH | 10 | 0.178 | 0.527 |
| 8 | 1 | 812 | 10.8 | 0.270 | 9.0 | 0.169 | 1.60 | KOH | 16 | 0.285 | 1.686 |
| 9 | 1 | 812 | 10.8 | 0.270 | 9.0 | 0.169 | 1.60 | LiOH | 8 | 0.334 | 1.976 |
| 10 | 1 | 812 | 10.8 | 0.270 | 9.0 | 0.169 | 1.60 | MgO | 10 | 0.496 | 2.935 |
| 11 | 2 | 1075 | 14.4 | 0.360 | 12.0 | 0.225 | 1.60 | Sr(OH)$_2$ | 10 | 0.075 | 0.333 |
| 12 | 3 | 562 | 21.6 | 0.540 | 9.0 | 0.169 | 3.20 | Ca(OH)$_2$ | 10 | 0.270 | 1.598 |
| 13 | 4 | 1190 | 43.2 | 1.080 | 9.0 | 0.169 | 6.39 | Ba(OH)$_2$ | 10 | 0.063 | 0.373 |
| 14 | 5 | 1060 | 21.6 | 0.540 | 9.0 | 0.169 | 3.20 | Ba(OH)$_2$ | 10 | 0.063 | 0.373 |
| 15 | 6 | 1000 | 10.8 | 0.270 | 9.0 | 0.169 | 1.60 | Ba(OH)$_2$ | 10 | 0.063 | 0.373 |
| 16 | 7 | 1050 | 8.1 | 0.203 | 9.0 | 0.169 | 1.20 | Ba(OH)$_2$ | 10 | 0.063 | 0.373 |
| 17 | 8 | 834 | 8.1 | 0.203 | 9.0 | 0.169 | 1.20 | Ba(OH)$_2$ | 10 | 0.063 | 0.373 |
| 18 | 9 | 1132 | 5.4 | 0.135 | 9.0 | 0.169 | 0.80 | Ba(OH)$_2$ | 10 | 0.063 | 0.373 |

Example 19 (for comparison)

The procedure followed was in accordance with the general description of the preparation of the catalysts, and 1,000 ml of support No. 1 (see Table 1) were impregnated with 366 ml of an aqueous solution containing 21.6 g, corresponding to 0.54 gram equivalent, of NaOH, dried to constant weight and then impregnated with 366 ml of an aqueous sodium tetrachloropalladate-(II) solution containing 18 g of palladium, corresponding to 0.338 gram equivalent, and transferred to a closable vessel. After a reaction time of 2 hours, the catalyst was washed free from alkali and dried and then reduced with hydrogen gas. The catalyst thus corresponded to the catalyst of Examples 4 and 7 (see Table 2), but lacked the alkali after-treatment according to the invention.

Example 20 (for comparison)

1,000 ml of lithium/aluminium spinel support described in DE-OS (German Published Specification) 2,045,882 in Example 1, having a BET surface area of 25 m$^2$/g, were impregnated with a volume, corresponding to its absorbency, of an aqueous sodium tetrachloropalladate-(II) solution containing 18 g of palladium, and was covered, in a beaker, with 400 ml of an aqueous solution containing 10% of hydrazine hydrate. After a reaction time of 2 hours, the catalyst was washed in a flowing stream of distilled water and was dried.

The catalyst thus prepared, containing palladium, contained the palladium in an irregular distribution within the individual spheres of catalyst, every transition between annular deposition on the surface of the catalyst and complete impregnation into the interior of the spheres being present.

After drying, the catalyst containing palladium was impregnated with a volume of an aqueous solution containing 10 g of KOH, corresponding to its absorbency, and was dried.

The finished catalyst contained 18 g of palladium and 10 g of KOH per liter of Li/Al spinel support. The amount of KOH present in the catalyst corresponded to an equivalence ratio (g. equivalent of base:g. equivalent of palladium) of 0.527.

Examples 21–34

A single-tube hydrogenation reactor (tube diameter 4 cm, tube length 80 cm) was charged to each case with one liter of catalyst. The activation of the catalyst was carried out in a stream of hydrogen at a temperature of 180° C. The temperature of the reactor was then adjusted to a value between 130° and 170° C. When this temperature had been reached, phenol was vaporized into the hydrogen stream at a temperature of approximately 160° C. The phenol/hydrogen mixture (phenol:-hydrogen molar ratio=1:6 to 1:15) flowed upward through the reactor. The loading was kept at 0.3 to 0.5 l of phenol per hour and per liter of catalyst. The gaseous reaction product was condensed after leaving the reactor. The composition of the product mixture was determined after a running time of 24 hours in each case. The details can be seen in Table 3.

The column "catalyst service life" in Table 3 indicates the period of time within which the product mixture contained over 90% by weight of cyclohexanol. Examples 33 and 34 are comparison examples.

TABLE 3

| Example No. | Materials fed in | | | Reaction temperature (°C.) | Composition of product | | By-Products (% by weight) | Catalyst service life (hrs.) |
|---|---|---|---|---|---|---|---|---|
| | Catalyst From Example No. | Phenol (l/hr.) | Hydrogen (mol per mol of plenol) | | Cyclohexanol (% by weight) | Cyclohexanone (% by weight) | | |
| 21 | 1 | 0.3 | 10.5 | 130 | 98.8 | 1.1 | 0.1 | 1270 |
| 22 | 2 | 0.3 | 10.5 | 130 | 94.7 | 4.7 | 0.6 | 740 |
| 23 | 3 | 0.3 | 10.5 | 160 | 93.8 | 5.8 | 0.4 | 520 |
| 24 | 4 | 0.3 | 10.5 | 140 | 98.4 | 1.1 | 0.5 | 1120 |
| 25 | 5 | 0.3 | 11.0 | 140 | 98.2 | 1.6 | 0.2 | 1180 |
| 26 | 6 | 0.5 | 10.5 | 130 | 99.0 | 0.9 | 0.1 | 630 |
| 27 | 7 | 0.3 | 9.0 | 150 | 96.0 | 3.8 | 0.3 | 610 |
| 28 | 8 | 0.4 | 11.0 | 130 | 98.1 | 1.6 | 0.3 | 480 |
| 29 | 9 | 0.3 | 10.5 | 140 | 97.9 | 2.0 | 0.1 | 1060 |
| 30 | 10 | 0.3 | 10.5 | 130 | 94.3 | 5.2 | 0.5 | 240 |
| 31 | 11 | 0.3 | 11.0 | 140 | 95.2 | 4.5 | 0.3 | 550 |
| 32 | 12 | 0.2 | 10.0 | 170 | 93.9 | 5.5 | 0.6 | 520 |
| 33 | 19 | 0.3 | 10.5 | 140 | 75.5 | 23.7 | 0.8 | — |

TABLE 3-continued

| Example No. | Materials fed in | | | Reaction temperature (°C.) | Composition of product | | By-Products (% by weight) | Catalyst service life (hrs.) |
|---|---|---|---|---|---|---|---|---|
| | Catalyst From Example No. | Phenol (l/hr.) | Hydrogen (mol per mol of plenol) | | Cyclohexanol (% by weight) | Cyclohexanone (% by weight) | | |
| 34 | 20 | 0.3 | 11.0 | 140 | 14.1 | 79.4 | 6.5 | — |

Example 35

The procedure followed was in general as described for Examples 21 to 34, but m-cresol was employed instead of phenol. The catalyst employed was that of Example 1. The reaction temperature was 150° C., the loading was 0.3 l of m-cresol per hour and per liter of catalyst, and the m-cresol:hydrogen molar ratio was 1:10. The composition of the product mixture was determined after a running time of 20 hours. It contained 92.2% by weight of methylcyclohexanol, 7.0% by weight of methylcyclohexanone and 0.8% by weight of by-products. The service life of the catalyst, that is to say the time until the content of methylcyclohexanol in the reaction product had fallen to less than 90%, was 730 hours.

Example 36 (for comparison)

The procedure followed was as in Example 35, but the catalyst employed was the catalyst from Example 19 which had not been subjected to after-treatment with a base. After 20 hours, the product mixture contained 31.7% by weight of methylcyclohexanol, 67.8% by weight of methylcyclohexanone and 0.5% by weight of by-products.

It will be understood that the specification and examples are illustrative but not limitative of the present invention and that other embodiments within the spirit and scope of the invention will suggest themselves to those skilled in the art.

What is claimed is:

1. A supported catalyst useful in the hydrogenation of optionally substituted phenols to give cyclohexanols prepared by, successively:
    (a) impregnating an inert support material having a BET surface area less than 20 m²/g with a base until saturation is reached,
    (b) drying the base impregnated support material to constant weight,
    (c) impregnating the dried base impregnated support material with a solution of a palladium compound until saturation is reached,
    (d) washing the base and palladium compound impregnated support material with water until ions from the base and anions of the palladium compound can no longer be detected in the wash water, and
    (e) drying the washed supported catalyst and thereafter;
    (f) doping the supported catalyst by applying a base to the washed and dried supported catalyst in a quantity such that the supported catalyst obtained therefrom contains 0.01 to 50 g equivalents of base per gram equivalent of palladium,
    (g) drying the base doped supported catalyst to constant weight and
    (h) reducing the deposited palladium compound to the metal at any desired point in time after carrying out stage (c) and before carrying out the reaction to be catalyzed by means of the catalyst, and if carrying out this reduction after stage (f), doing so under conditions in which the base applied in stage (f) remains on the supported catalyst wherein the support material is selected from aluminum oxides, silicon dioxides, silicon dioxide/aluminum oxide mixtures, amorphous silicas, kieselguhrs, mixtures thereof optionally containing, in addition, silicon dioxides or aluminum oxides, titanium oxides, zirconium oxides, magnesium oxides, magnesium silicates, zirconium silicates, magnesium/aluminum spinels, silicon carbides, tungsten carbides, mixtures of silicon carbides with silicon dioxides or any desired mixtures of the abovementioned materials.

2. A supported catalyst according to claim 1 wherein the base in stage (a) is selected from an oxide, carbonate, bicarbonate, hydrogen phosphate, hydroxide, alkoxid, formate, alkali metal silicate, alkali metal aluminate or mixtures thereof; and using, in stage (c) an aqueous solution of $Na_2[PdCl_4]$, $PdCl_2$ and/or $Pd(NO_3)_2$ in a concentration such that 1 to 20 g of palladium is applied to the support by means of a single impregnation.

3. A supported catalyst according to claim 1, wherein the base applied in stage (f) is selected from oxides, hydroxides, alkoxides, carbonates, bicarbonates, hydrogenphosphates, formates, silicates and/or aluminates of alkali and/or alkaline earth metals.

4. A supported catalyst according to claim 1, wherein the reduction is carried out with hydrazine hydrate, hydrogen, formaldehyde or sodium borohydride in the event that stage (h) is carried out before stage (f) and wherein the reduction is carried out with hydrogen in the event that stage (h) is carried out after stage (f).

5. A process for the preparation of a supported catalyst, comprising, successively:
    (a) impregnating an inert support material having a BET surface area less than 20 m²/g with a base until saturation is reached,
    (b) drying the base impregnated support material to constant weight,
    (c) impregnating the dried based impregnated support material with a solution of a palladium compound until saturation is reached,
    (d) washing the base and palladium compound impregnated support material with water until ions from the base and anions of the palladium compound can no longer be detected in the wash water, and
    (e) drying the washed supported catalyst and thereafter;
    (f) doping the supported catalyst by applying a base to the washed and dried supported catalyst in a quantity such that the supported catalyst obtained therefrom contains 0.01 to 50 g equivalents of base per gram equivalent of palladium,
    (g) drying the base doped supported catalyst to constant weight and
    (h) reducing the deposited palladium compound to the metal at any desired point in time after carrying out stage (c) and before carrying out the reaction to be catalyzed by means of the catalyst, and if carrying out this reduction after stage (f), doing so under conditions in which the base applied in stage (f), doing so under conditions in which the base applied in stage (f) remains on the supported catalyst wherein the support material is selected from aluminum oxides, silicon dioxides, silicon dioxide/aluminum oxide mixtures, amorphous silicas, kieselguhrs, mixtures thereof optionally containing, in addition, silicon dioxides or aluminum oxides, titanium oxides, zirconium oxides, magnesium oxides, magnesium silicates, zirconium silicates, magnesium/aluminum spinels, silicon carbides, tungsten carbides, mixtures of silicon carbides with silicon dioxides or any desired mixtures of the abovementioned materials.

6. A supported catalyst according to claim 1, wherein the support material is $\alpha$-$Al_2O_3$ and the base employed in stage (f) is barium hydroxide.

* * * * *